United States Patent
Shi et al.

(10) Patent No.: US 10,206,982 B2
(45) Date of Patent: Feb. 19, 2019

(54) WOUND DEBRIDEMENT COMPOSITIONS CONTAINING SEAPROSE AND METHODS OF WOUND TREATMENT USING SAME

(71) Applicant: SMITH & NEPHEW ORTHOPAEDICS AG, Baar (CH)

(72) Inventors: Lei Shi, Mansfield, TX (US); Aleksa Jovanovic, Fort Worth, TX (US); Dennis Carson, Burleson, TX (US)

(73) Assignee: SMITH & NEPHEW ORTHOPAEDICS AG, Baar (CH)

(*) Notice: Subject to any disclaimer, the term of this patent is extended or adjusted under 35 U.S.C. 154(b) by 0 days.

(21) Appl. No.: 15/417,680

(22) Filed: Jan. 27, 2017

(65) Prior Publication Data

US 2017/0136103 A1    May 18, 2017

Related U.S. Application Data

(63) Continuation of application No. 14/116,728, filed as application No. PCT/US2012/037480 on May 11, 2012.

(60) Provisional application No. 61/485,503, filed on May 12, 2011.

(51) Int. Cl.
| | |
|---|---|
| A61K 38/48 | (2006.01) |
| A61K 9/00 | (2006.01) |
| A61K 9/06 | (2006.01) |
| A61K 47/06 | (2006.01) |
| A61K 47/10 | (2017.01) |
| A61K 47/38 | (2006.01) |
| A61K 47/44 | (2017.01) |

(52) U.S. Cl.
CPC .......... *A61K 38/482* (2013.01); *A61K 9/0014* (2013.01); *A61K 9/0019* (2013.01); *A61K 9/06* (2013.01); *A61K 47/06* (2013.01); *A61K 47/10* (2013.01); *A61K 47/38* (2013.01); *A61K 47/44* (2013.01); *C12Y 304/21063* (2013.01)

(58) Field of Classification Search
None
See application file for complete search history.

(56) References Cited

U.S. PATENT DOCUMENTS

| | | | |
|---|---|---|---|
| 4,197,291 A * | 4/1980 | Klein | C12N 9/50 424/94.65 |
| 5,902,600 A | 5/1999 | Woller et al. | 424/445 |
| 6,172,219 B1 | 1/2001 | Callegaro et al. | 536/123.1 |
| 6,399,092 B1 | 6/2002 | Hobson et al. | 424/443 |
| 6,479,060 B1 | 11/2002 | Jones et al. | 424/401 |

(Continued)

FOREIGN PATENT DOCUMENTS

| | | |
|---|---|---|
| EP | 0590746 | 9/1993 |
| JP | 56092217 | 7/1981 |

(Continued)

OTHER PUBLICATIONS

Luisetti et al., Int. J. Tiss. Reac. 13(4): 187-192 (1991).*

(Continued)

*Primary Examiner* — Erin M. Bowers
(74) *Attorney, Agent, or Firm* — Norton Rose Fulbright US LLP

(57) ABSTRACT

Wound debridement compositions containing the proteolytic enzyme Seaprose and use of such compositions in wound treatment for the enzymatic debridement of wounds.

15 Claims, 2 Drawing Sheets

(56) References Cited

U.S. PATENT DOCUMENTS

| | | | |
|---|---|---|---|
| 6,548,556 B2 | 4/2003 | Hobson et al. | 514/772.4 |
| 7,294,497 B2 | 11/2007 | Kaplan | 435/200 |
| 7,459,155 B2 | 12/2008 | Margolin et al. | 424/94.64 |
| 7,642,079 B2 | 1/2010 | Cayouette et al. | 435/212 |
| 7,785,584 B2 | 8/2010 | Jones et al. | 424/94.65 |
| 8,066,991 B2 | 11/2011 | Jolly | 424/94.65 |
| 8,119,124 B2 | 2/2012 | Gorecki et al. | 424/94.2 |
| 8,383,101 B2 | 2/2013 | Olmstead | 424/94.2 |
| 8,632,769 B2 | 1/2014 | Barron | 424/94.1 |
| 8,809,031 B2 | 8/2014 | England et al. | 435/202 |
| 2003/0026794 A1 | 2/2003 | Fein | 424/94.2 |
| 2003/0027310 A1 | 2/2003 | Berka et al. | 435/196 |
| 2003/0198631 A1 | 10/2003 | Shi et al. | 424/94.63 |
| 2003/0198632 A1 | 10/2003 | Shi et al. | 424/94.63 |
| 2005/0158299 A1 | 7/2005 | Margolin et al. | 424/94.63 |
| 2007/0264715 A1 | 11/2007 | Robinson et al. | 435/471 |
| 2010/0124549 A1 | 5/2010 | Studin | 424/94.65 |
| 2010/0221237 A1 | 9/2010 | Kokai-Kun et al. | 424/94.67 |
| 2010/0254968 A1 | 10/2010 | Desser et al. | 424/94.64 |
| 2012/0258089 A1 | 10/2012 | Madhyastha et al. | 424/94.61 |

FOREIGN PATENT DOCUMENTS

| | | |
|---|---|---|
| JP | H06262165 | 9/1994 |
| JP | 2008290966 | 12/2008 |
| WO | WO 2002/051436 | 7/2002 |
| WO | WO 2005/018695 * | 3/2005 |
| WO | WO 2005/115357 | 12/2005 |
| WO | WO 2006/037606 | 4/2006 |
| WO | WO 2008/019417 | 2/2008 |
| WO | WO 2010/079209 | 7/2010 |
| WO | WO 2010/112848 | 10/2010 |
| WO | WO 2011/063394 | 5/2011 |
| WO | WO 2011/071986 | 6/2011 |
| WO | WO 2012/155027 | 11/2012 |
| WO | WO 2014/145037 | 9/2014 |

OTHER PUBLICATIONS

Akiyama et al., "Recent Investigations of *Staphylococcus aureus* in Dermatology", Japanese journal of Dermatology, 109(13), 1999, pp. 2095-2102. (English Abstract).

Barbera et al., "Multicentre clinical study on seaprose S in acute and chronic respiratory inflammation", Minerva Cardioangiol, 35(4):49-156, 1996.

Bracale and Selvetella, "Clinical study of the efficacy of and tolerance to seaprose S in inflammatory venous disease. Controlled study versus serration-peptidase", Minerva Cardioangiol, 44(10):515-524, 1996.

Braga et al., "Effects of Seaprose on the Rheology of Bronchial Mucus in Patients with Chronic Bronchitis. A Double-Blind Study vs. Placebo", Int. J. Clin. Pharm. Res., 8(3):179-185, 1993.

Braga et al., "In Vitro Rheological Assessment of Mucolytic Activity Induced by Seaprose", Pharmacological Research, 22(5):611-617, 1990.

Dindelli et al., "Clinical efficacy and safety of Seaprose S in the treatment of surgical wound complications in puerperium", Minerva Cardioangiol, 42(7-8):313-315, 1990.

Drug Information Sheet; Teoase Tablets, 15mg, Revised Mar. 2008, 1 page.

Enzyme Handbook, Springer-Verlag Berlin Heidelber, 1998, 1-8.

Fossati, "Antiinflammatory Effects of Seaprose-S on Various Inflammation Models", Drugs Exptl. Clin. Res., 25(6):263-270, 1999.

International Preliminary Report on Patentability issued in PCT Application No. PCT/US2012/037480, dated Nov. 21, 2013.

International Search Report and Written Opinion issued in PCT Application No. PCT/US2012/037480, dated Jul. 16, 2012.

Luisetti et al., "Some Properties of the Alkaline Proteinase From *Aspergillus Melleus*", Int. J. Tiss. Reac., 13(4):187-192, 1991.

Miyazaki et al., "The Effect of SA-001 (Jeoase) on the Pharyngolaryngeal Complications Following Endotracheal Anesthesia", Masui (Anesthesia), 18(8):722-730, 1969.

Moretti et al., "Effects of Seaprose on Sputum Biochemical Components in Chronic Bronchitic Patients: A Double-Blind Study vs. Placebo", Int. J. Clin. Phar. Res, 8(5):275-280, 1993.

Morihara, K. et al.: "Comparative study of various serine alkaline proteinases from microorganisms. Esterase activity against N-acylated peptide ester substrates", Archives of Biochemistry and Biophysics, vol. 165, (1974), pp. 72-79.

Nakatani et al., "Interaction of Asp. Melleus Semi-alkaline protease with benzeneboronic acid", J. Biochem, 81(5):1296-1272, 1977.

Notice of Reasons for Rejection (Translation) dated Mar. 15, 2017, issued in corresponding Japanese application No. 2015-511734.

Ogawa et al., "The Evaluation of the Effect of Bromelain Ointment on the Debridement of Eschar of Burn, Decubitus and Various Wound", Journal of New Remedies & Clinics, 48(10), 1999, pp. 1301-1309. (English Abstract).

Sasaki, Database WPI, Tomson Scientific, XP-002678257, Dec. 4, 2008.

Shi et al., "Evaluation of Wound Debridement Efficacy of Proteolytic Enzymes From the Fungus *Aspergillus melleus*", Wound Repair and Regeneration, 20(2), 2012, pp. A39. (Abstract Only).

Spadari et al., "Highly Restricted Specificity of the Serine Proteinase Aspergillopeptidase B", Biochmica et Biophysica Acta, 359:267-272, 1974.

Turkova et al., "Alkaline Proteinases of the Genus *Aspergillus*", Biochimica et Biophysica Acta, 257:257-263, 1972.

James et al., "Biofilms in Chronic Wounds," *Wound Repair Regen*, 2008, 16:37-44.

Kiedrowski et al., "New approaches for treating staphylococcal biofilm infections,"*Ann. N.Y. Acad. Sci.*, 2011, 1241:104-121.

Falanga, Vincent, "Wound Bed Preparation and the role of Enzymes; A Case for Multiple actions of Therapeutic Agents," *Wounds*, 2002; 14(2): 47-50.

Ohjimi, "Wounds and Infection—Clinical Conditions and Diagnosis of Wound Infections and Therapeutic Strategies Therefors," *Plastic and Reconstructive Surgery Today*, 2010; 6: 1-5.

Tiwari, V., "Burn Wound: How it Differs from Other Wounds?" *Indian Journal of Plastic Surgery*, 2012; 45(2):364-373.

Braga et al., "The influence of seaprose on erythromycin penetration into bronchial mucux bronchopulmonary infections," *Drugs Exp. Clin. Res.* 1992; 18(3): 105-111 (Abstract only).

* cited by examiner

WOUND DEBRIDEMENT COMPOSITIONS CONTAINING SEAPROSE AND METHODS OF WOUND TREATMENT USING SAME

CROSS REFERENCE TO RELATED APPLICATIONS

This application is a continuation of U.S. patent application Ser. No. 14/116,728, filed Nov. 8, 2013, which is a national phase application under 35 U.S.C. § 371 of International Patent Application No. PCT/US2012/037480 filed May 11, 2012, which claims the benefit of U.S. Provisional Application No. 61/485,503, filed May 12, 2011. The contents of the referenced applications are incorporated into the present application by reference.

BACKGROUND OF THE INVENTION

A. Field of the Invention

The present invention generally relates to methods and compositions useful for the debridement and treatment of wounds. More specifically, the present invention is related to enzymatic wound debridement compositions comprising Seaprose and methods of wound treatment using same.

B. Background of the Invention

The healing of wounds is a complex process which is often further complicated by the presence of nonviable necrotic tissue in the wound area. The presence of eschar and other necrotic tissue in a wound can impede the healing process causing the wound to become a slow-healing or "chronic" wound. Wounds such as diabetic foot ulcers, venous leg ulcers, arterial leg ulcers, decubitus ulcers, stasis ulcers, dermal ulcers, burns, and pressure ulcers are examples of wounds which can become chronic wounds with the presence of necrotic tissue that delays healing, and these wounds can be inhibited from healing.

Effective wound cleansing and debridement are long recognized prerequisites for optimal wound healing. Necrotic tissue present in a wound bed is undesirable because it may serve as a reservoir for bacterial growth, contain elevated levels of inflammatory mediators that promote chronic inflammation at the wound site, and impair cellular migration necessary for wound repair. It is increasingly well recognized that clearing a wound bed of necrotic tissue is an important step that may facilitate the healing process for a variety of wound types, particularly burn wounds and various chronic wounds.

A number of different modalities exist for wound debridement. The four most common debridement methods are surgical, autolytic, enzymatic, and mechanical. Each of these has its own benefits and shortcomings, depending on the wound type and the condition of the patient.

Enzymatic debridement is the process of topically applying an enzymatic debridement agent to the wound to digest eschar and other necrotic tissue, thereby facilitating removal of the necrotic tissue. Enzymatic debridement agents are those enzymes that can rapidly digest necrotic tissue without injury to living cells, thereby speeding the healing processes. Use of such debridement agents have included the employment of a wide variety of microbial, plant and animal materials, even things such as maggots or blowfly larvae, but more commonly, the enzyme papain derived from the papaya tree, the enzyme trypsin derived from animal pancreas, and the enzyme collagenase derived from the bacteria *Clostridium histolyticum*. The mechanism in almost all of these cases has been identified with enzymatic activity.

Healing of wounds is delayed by the presence of pus, tissue debris, bacteria, exudates and eschar. The major constituents of wound eschar are proteins, such as collagen, fibrin, elastin, fibronectin, and hemoglobin. Of these, various types of wound eschar have been demonstrated to be predominantly composed of the fibrous proteins collagen, elastin, and fibrin. The primary purpose of the debridement enzyme is to clean a wound of all of the various necrotic tissue elements and to thin out thick exudative secretions. When properly applied to selected patients, certain proteolytic enzymes cleanse infected proteinous surfaces of their inflammatory exudate without harm to living tissues, facilitate the drainage of areas of local purulent, sanguineous and fibrinous accumulations, promote the liberation of hidden bacteria, thereby exposing them to antimicrobial agents and native immune forces, and increase the rate of repair of previously infected wounds. This enzymatic action can also be of benefit for the treatment of inflammatory skin diseases such as psoriasis and eczema.

Topical ointment and cream compositions containing proteolytic enzymes such as papain, trypsin, and collagenase have been widely employed for enzymatic wound debridement particularly in patient populations not amenable to surgical debridement. Compositions containing thermolysin (US patent application 2003/0198631) and bromelain (U.S. Pat. No. 4,197,291) have also been disclosed for use in wound debridement.

An example of a commercially available enzymatic debridement ointment is one containing a bacterially derived collagenase used to degrade collagen components in wounds. Another product is one containing fibrinolysin which is specifically used to digest fibrin debris. These products contain enzymes that are potent and specific for their substrates. Such high debridement specificity results in less harm to viable tissue and less irritation to patients. However, since these enzymes are substrate specific, debridement of nonviable necrotic tissue may be slow or incomplete because of the various protein elements present in necrotic tissue of chronic wounds. For example, collagenase is very specific to digest collagens, but not very effective for other proteins. Likewise, fibrinolysin is specifically used to digest fibrin debris, but not very effective for other proteins.

Because of the diversity of proteins in wound eschar and other necrotic tissue, commercially available compositions containing nonspecific proteases, such as papain, were used for wound debridement with good clinical efficacy. However, most of these products are grandfathered (DESI) drugs and are no longer commercially available.

SUMMARY OF THE INVENTION

The present invention is generally directed to wound debridement compositions containing the proteolytic enzyme Seaprose and methods of wound treatment for the enzymatic debridement of wounds with such compositions. Such wounds being treated or debrided with the compositions of the present invention can include necrotic tissue (e.g., eschar).

In one aspect of the present invention, there is disclosed a method of treating a wound comprising topically applying to the wound a composition comprising Seaprose, wherein the wound is in need of debridement. The wound can be present on a person's skin (e.g., the epidermal and/or dermal layer of the skin can be damaged). The wound can include necrotic tissue (e.g., eschar). In another aspect, the amount of Seaprose is a wound debridement effective amount of Seaprose. In one embodiment, the composition further comprises a pharmaceutically acceptable topical carrier. In one embodiment, the wound is a chronic wound. In various embodiments, the chronic wound is a diabetic foot ulcer, a venous leg ulcer, an arterial leg ulcer, a decubitus ulcer, a stasis ulcer, a dermal ulcer, a burn, or a pressure ulcer.

In another aspect of the present invention, there is disclosed a method of enzymatic wound debridement comprising topically applying to a wound in need of debridement a composition comprising a debridement effective amount of Seaprose. Again, the wound can be present on a person's skin (e.g., the epidermal and/or dermal layer of the skin can be damaged). The wound can include necrotic tissue (e.g., eschar). In one embodiment, the composition further comprises a pharmaceutically acceptable topical carrier. In one embodiment, the wound is a chronic wound. In various embodiments, the chronic wound is a diabetic foot ulcer, a venous leg ulcer, an arterial leg ulcer, a decubitus ulcer, a stasis ulcer, a dermal ulcer, a burn, or a pressure ulcer. The wound can include necrotic tissue (e.g., eschar).

In yet another aspect of the present invention, there is disclosed a method of treating a wound comprising injecting into the wound a composition comprising Seaprose, wherein the wound is in need of debridement. The wound can be present on a person's skin (e.g., the epidermal and/or dermal layer of the skin can be damaged). The wound can include necrotic tissue (e.g., eschar). In another aspect, the amount of Seaprose is a wound debridement effective amount of Seaprose. In one embodiment, the composition further comprises a pharmaceutically acceptable carrier suitable for injection. In one embodiment, the wound is a chronic wound. In various embodiments, the chronic wound is a diabetic foot ulcer, a venous leg ulcer, an arterial leg ulcer, a decubitus ulcer, a stasis ulcer, a dermal ulcer, a burn, or a pressure ulcer.

In still another aspect of the present invention, there is disclosed a method of enzymatic wound debridement comprising injecting into a wound in need of debridement a composition comprising a debridement effective amount of Seaprose. The wound can be present on a person's skin (e.g., the epidermal and/or dermal layer of the skin can be damaged). The wound can include necrotic tissue (e.g., eschar). In one embodiment, the composition further comprises a pharmaceutically acceptable carrier suitable for injection. In one embodiment, the wound is a chronic wound. In various embodiments, the chronic wound is a diabetic foot ulcer, a venous leg ulcer, an arterial leg ulcer, a decubitus ulcer, a stasis ulcer, a dermal ulcer, a burn, or a pressure ulcer.

In another aspect of the present invention, there is disclosed a composition for the debridement of wounds comprising a wound debridement effective amount of Seaprose and a pharmaceutically acceptable carrier for topical application to the wound or for injection into the wound. The wound can be present on a person's skin (e.g., the epidermal and/or dermal layer of the skin can be damaged). The wound can include necrotic tissue (e.g., eschar).

In one embodiment, the compositions of the present invention are sterile. In one embodiment, the Seaprose is in a dissolved state in the pharmaceutically acceptable carrier. In another embodiment, the Seaprose is in a dispersed state in the pharmaceutically acceptable carrier. Further, the Seaprose can be isolated or purified Seaprose. Also, the wound debridement capabilities of the compositions of the present invention can be used in lieu of surgical removal of necrotic tissue.

Unless otherwise specified, the percent values expressed herein are weight by weight and are in relation to the total composition.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the transitional phase "consisting essentially of," in one non-limiting aspect, a basic and novel characteristic of the compositions and methods disclosed in this specification includes the compositions' enhanced enzymatic debridement activity.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

The term "effective," as that term is used in the specification and/or claims, means adequate to accomplish a desired, expected, or intended result.

Figure 1:
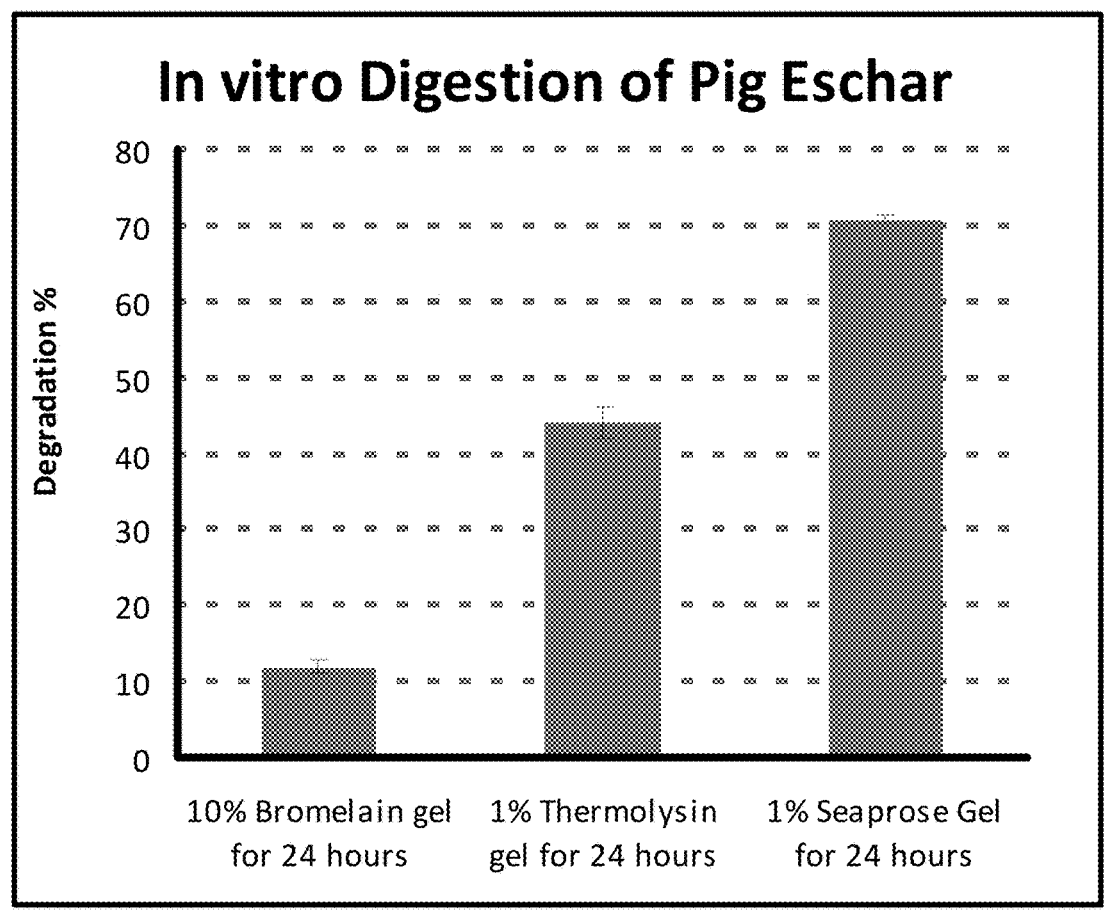
FIG. 1. A plot of the results of an in-vitro study comparing the degradation of pig eschar by bromelain, thermolysin, and Seaprose gels at 37° C. within a 24-hour period.

DESCRIPTION OF ILLUSTRATIVE
EMBODIMENTS

The present invention is directed to enzymatic wound debridement compositions comprising Seaprose and methods of wound treatment and enzymatic wound debridement using same.

A. Compositions

The compositions of the present invention are compositions for the debridement of wounds comprising a debridement effective amount of Seaprose and can further comprise a pharmaceutically acceptable carrier. The compositions of the invention may include Seaprose as the sole ingredient or also include a pharmaceutically acceptable carrier. The compositions of the invention may further comprise pharmaceutically active ingredients, cosmetically active ingredients, and vulnerary agents (e.g., growth factors) suitable for topical or injectable administration to wounds.

In-vitro studies demonstrated that a composition containing Seaprose was surprisingly more effective in digesting eschar material (FIG. 1) than were compositions of bromelain and thermolysin.

1. Seaprose

Seaprose is a semi-alkaline protease produced by the fermentation of the fungus *Aspergillus melleus* and is commercially available in a powder form from Amano Enzyme, Inc., Japan under the trade name SEAPROSE S®. Seaprose may be prepared by either a liquid or solid fermentation process using techniques known by one of skill in the art. Seaprose has also been referred to as onoprose, promelase, promelasum, Jeoase, FLAMINASE® (Prodotti Formenti S.r.l., Milan Italy), and *Aspergillus melleus* semi-alkaline proteinase.

The major protease in Seaprose is a semi-alkaline protease with a molecular weight around 31 kDa. It can also contain other enzymes such as amylase, which is a hydrolytic enzyme which breaks down carbohydrates. Alternatively, Seaprose can be purified or isolated by standard techniques known to those of skill in the art. Seaprose shows great stability at an optimal pH range of from 5 to 9, and an optimal temperature below 50° C. These conditions are suitable for application of the enzyme in wounds and favorable for drug formulation and manufacture.

Seaprose has previously been used for a variety of medical indications and treatment; however, it has never previously been used in a topical or injectable form for use as a wound debriding agent. For example, Seaprose has been shown to possess in-vitro mucolytic activity (Braga 1990) and to effectively treat patients with bronchitis by oral administration of Seaprose capsules (Braga 1993), (Moretti 1993). Seaprose has shown anti-inflammatory activity against many different inflammatory conditions in animal models (Fossati 1991). Seaprose was shown to be effective in treating patients with inflammatory venous disease by oral administration of Seaprose tablets (Bracale 1996). Seaprose has been used to treat abdominal pain due to pancreatitis (U.S. Pat. No. 7,459,155). Seaprose has been used to treat complications of puerperal surgical wounds by oral administration of Seaprose 30 mg tablets (Dindelli 1990).

According to the present invention, Seaprose may be in a dissolved state and/or a dispersed state in the pharmaceutically acceptable carrier. The Seaprose may also be encapsulated. It may also be used neat without a carrier. Seaprose can also be used in a purified or isolated form.

The amount of Seaprose in a composition with a pharmaceutically acceptable carrier is an amount effective for wound debridement and can generally range from about 0.001% w/w to about 10% w/w; or from about 0.01% to about 9%; or from about 0.1% to about 8%; or from about 0.1% to about 0.9%; or from about 0.2% to about 0.8%; or from about 0.3% to about 0.7%; or from about 0.4% to about 0.6%; or about 0.5%; or from about 0.5% to about 7%; or about 1% to about 6%; or from about 1.5% to about 5%; or from about 0.5% to about 1.5%; or from about 0.6% to about 1.4%; or from about 0.7% to about 1.3%; or from about 0.8% to about 1.2%; or from about 0.9% to about 1.1%; or about 1%. Such amount will be that amount which effectively debrides necrotic tissue in wounds.

2. Pharmaceutically Acceptable Carriers

The compositions of the present invention may comprise various pharmaceutically acceptable carriers suitable for topical delivery and compatible with Seaprose. Non-limiting examples include lotions, creams, emulsions, ointments, gels, pastes, solutions, aerosol sprays, aerosol foams, non-aerosol sprays, non-aerosol foams, powders, liquid solutions, liquid suspensions, films, and sheets. The compositions may be impregnated in gauzes, bandages, or other wound dressing materials for topical delivery.

The compositions of the invention may further comprise functional ingredients suitable for use in topical compositions and compatible with Seaprose. Non-limiting examples include absorbents, antimicrobial agents, antioxidants, binders, buffering agents (including Tris buffer solutions), bulking agents, chelating agents, colorants, biocides, deodorant agents, emulsion stabilizers, film formers, fragrance ingredients, humectants, lytic agents, enzymatic agents, opacifying agents, oxidizing agents, pH adjusters, plasticizers, preservatives, reducing agents, emollient skin conditioning agents, humectant skin conditioning agents, moisturizers, surfactants, emulsifying agents, cleansing agents, foaming agents, hydrotopes, solvents, suspending agents, viscosity control agents (rheology modifiers), viscosity increasing agents (thickeners), and propellants. Listings and monographs of the functional ingredients described herein are disclosed in The International Cosmetic Ingredient Dictionary and Handbook (INCI), $12^{th}$ Edition, 2008, hereby incorporated by reference.

Suitable pharmaceutically acceptable topical carriers include an anhydrous hydrophilic wound debrider composition as disclosed in: U.S. Pat. No. 6,548,556 herein incorporated by reference; a spray-on topical wound debrider composition as disclosed in U.S. Pat. No. 7,785,584 herein incorporated by reference; an enzymatic wound debriding composition as disclosed in international PCT application PCT/US10/59409 herein incorporated by reference; a hydrogenated castor oil ointment as disclosed in U.S. Pat. No. 6,479,060 herein incorporated by reference; an anhydrous hydrophilic absorbent wound dressing as disclosed in U.S. Pat. No. 6,399,092 herein incorporated by reference; and a hydrogel wound dressing as disclosed in U.S. Pat. No. 5,902,600 herein incorporated by reference.

The compositions of the present invention may also comprise various pharmaceutically acceptable carriers suitable for injectable delivery compatible with Seaprose.

The compositions of the present invention may be packaged in any package configuration suitable for topical or injectable products. Non-limiting examples for topical products include bottles, lotion pumps, toddles, tubes, jars, non-aerosol pump sprayers, aerosol containers, syringes, pouches, and packets. The packages may be configured for single-use (one dose) or multiple-use administration. Non-limiting examples for injectable products include vials, syringes, micro-needle syringes, or bags.

The compositions of the present invention may also be sterile. They may be sterilized via an aseptic manufacturing process or sterilized after packaging by methods known in the art.

3. Manufacture

The compositions of the present invention may be manufactured by suitable processing methods known by one of skill in the art for topical and/or injectable products. For example, Seaprose can be admixed with the pharmaceutically acceptable carrier. Alternatively, Seaprose can be applied to a wound in a neat form (e.g., without carrier).

B. Methods of Use

The composition of the present invention may be used in methods of treatment for the debridement of wounds in need of debridement. The method comprises applying to the wound a composition comprising Seaprose either by topical application or by injection. After topical application, the wound may be covered with a wound dressing such as a gauze pad. The composition may be applied to a dressing such as a gauze pad first and then applied to the wound surface. The application amount depends on the severity and type of the wound and nature of the subject.

The composition can be applied to the wound periodically, for example, daily. A therapeutic regiment could be followed to include periodic dressing changes with wound cleansing and application of fresh composition between changes until the debridement of the necrotic tissue is complete. Use of the composition could also be discontinued when debridement of necrotic tissue is complete.

Burns, acute wounds, or chronic wounds may be treated according to the methods of the present invention. Non-limiting examples of chronic wounds include diabetic foot ulcers, venous leg ulcers, arterial leg ulcers, decubitus ulcers, stasis ulcers, dermal ulcers, burns, and pressure ulcers.

EXAMPLES

The following examples are included to demonstrate certain non-limiting aspects of the invention. It should be appreciated by those of skill in the art that the techniques disclosed in the examples which follow represent techniques discovered by the applicants to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Exemplary Formulations

The following Tables provide non-limiting examples of formulations containing Seaprose of the present invention:

TABLE 1

| Gel* | |
|---|---|
| Ingredient | % Concentration (by weight) |
| SEAPROSE S | 1.0 |
| Tris Buffer Solution 10 mM (pH 7.5) | 96.4 |
| Hydroxyethylcellulose (HEC) | 2.6 |
| TOTAL | 100 |

*Process: A gel was made with the HEC and Tris buffer. SEAPROSE S was admixed with the HEC gel. The viscosity of the gel gradually reduced over time possibly due to the amylase present in the Seaprose material degrading the HEC.

TABLE 2

| Gel* | |
|---|---|
| Ingredient | % Concentration (by weight) |
| SEAPROSE S | 1.0 |
| CURASOL ® Gel Wound Dressing | 99.0 |
| TOTAL | 100 |

*Process: SEAPROSE S was admixed with the CURASOL Gel Wound Dressing to form a clear gel. The viscosity was maintained over time.

TABLE 3

| Cream* | |
|---|---|
| Ingredient | % Concentration (by weight) |
| SEAPROSE S | 0.5 |
| Tris Buffer Solution 10 mM (pH 7.5) | 71.52 |
| Glycerin | 7.0 |

TABLE 3-continued

| Cream* | |
|---|---|
| Ingredient | % Concentration (by weight) |
| Methylparaben | 0.2 |
| Propylparaben | 0.08 |
| Emulsifying Wax | 15.2 |
| Isopropyl Palmiitate NF | 5.5 |
| TOTAL | 100 |

*Process: Methylparaben, propylparaben and glycerin were dissolved in the Tris buffer solution at 70° C. Emulsifying wax and isopropyl palmitate were added to the above solution at 70° C. and mixed to form an emulsion. The emulsion was cooled to 35° C. at which time SEAPROSE S was admixed with the emulsion. A white cream was obtained.

TABLE 4

| Ointment* | |
|---|---|
| Ingredient | % Concentration (by weight) |
| SEAPROSE S | 0.5 |
| White Petrolatum | 78.5 |
| PEG-600 | 20.0 |
| Poloxamer-407 | 1.0 |
| TOTAL | 100 |

*Process: An Active Phase was made by melting a mixture of half of the amount of PEG-600 and half of the amount of poloxamer-407 at 70° C., cooling the mixture to 35° C. at which time SEAPROSE S was admixed with the mixture. A Main Phase was made by melting a mixture of white petrolatum and the remaining half of the amount of PEG-600, and the remaining half of the amount of poloxamer-407 at 70° C., cooling the mixture to 35° C. The Active Phase was then admixed with the Main Phase. The resulting mixture was mixed at RT for 45 minutes.

Example 2

In Vitro Digestion of Pig Burn Eschar

The gel formula in Table 1 (1% Seaprose Gel) and each of the following two gel formulas (1% Thermolysin Gel and 10% Bromelain Gel) were used in an in-vitro study to compare the degradation of pig eschar by each gel formula.

TABLE 5

| 1% Thermolysin Gel | |
|---|---|
| Ingredient | % Concentration (by weight) |
| Thermolysin (Sigma-Aldrich) | 1.0 |
| Tris Buffer Solution 10 mM (pH 7.5) | 95.1 |
| Hydroxyethylcellulose (HEC) | 2.9 |
| Sodium Chloride | 0.9 |
| Calcium Chloride | 0.1 |
| TOTAL | 100 |

TABLE 6

| 10% Bromelain Gel | |
|---|---|
| Ingredient | % Concentration (by weight) |
| Bromelain (Spectrum) | 10.0 |
| Water | 84.6 |
| Carbomer 980K | 1.9 |
| Disodium Phosphate | 2.6 |
| 4-Chloro-3-Methylphenol | 0.1 |
| Sodium Hydroxide | 0.8 |
| TOTAL | 100 |

The study was conducted in-vitro using eschar materials obtained from pig burn wounds. The eschar materials were dried completely. The dry weight was used as baseline. Samples of the dried eschar weighing 40-60 mg were moisturized with 50 μl of Tris buffered saline. The moisturized eschar samples were immersed in 3 g of each of the three gel formulas. The gels with eschar were stored at 37° C. for 24 hours. After 24 hours, the samples were centrifuged at 5000 rpm for 5 minutes. The supernatant was discarded and water was added to wash the precipitates. The samples were centrifuged again. Another wash step was performed and then the precipitates were freeze-dried. The dry weights of the precipitates were used to calculate the degradation percentage based on the baseline dry weights. The results are presented in FIG. 1.

The results in FIG. 1 demonstrate that the Seaprose gel was more effective and exhibited superior potency in digesting the eschar material as compared to the 1% thermolysin gel (Table 5) and 10% bromelain gel (Table 6) within the 24 hour period. The quickness at which the Seaprose gel digested the eschar as compared to the 1% thermolysin gel and the 10% bromelain gel was totally unexpected, because thermolysin and bromelain are both known in the art to be a fast debriding enzymes (see, e.g., U.S. Patent Publication 2003/0198631 and U.S. Pat. No. 8,119,124, respectively). The results of the in-vitro study indicate that Seaprose can efficiently and effectively target and digest eschar proteins and therefore, it is suitable as a superior enzymatic wound debrider which can be used for the treatment of wounds in need of debridement.

Example 3

In Vivo Debridement of Pig Burn

Figure 2:
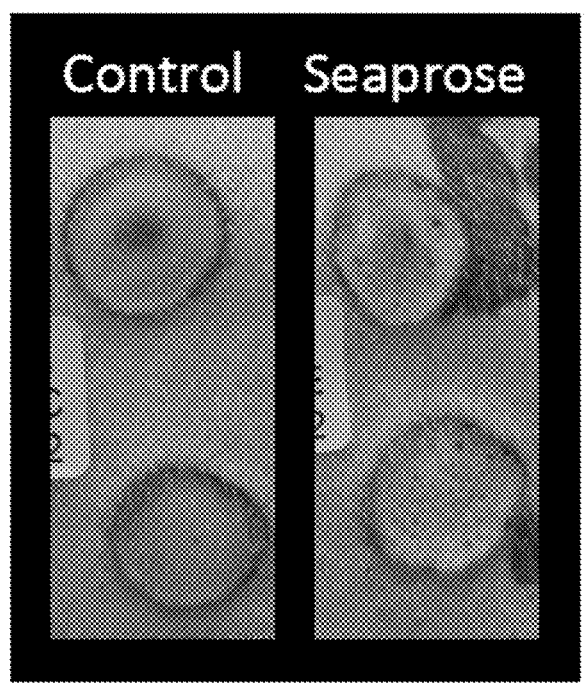
FIG. 2. An image of in vivo pig wounds after 24 hour treatment with a Seaprose hydrogel compared with a control (moist wound care).
Figure 3:
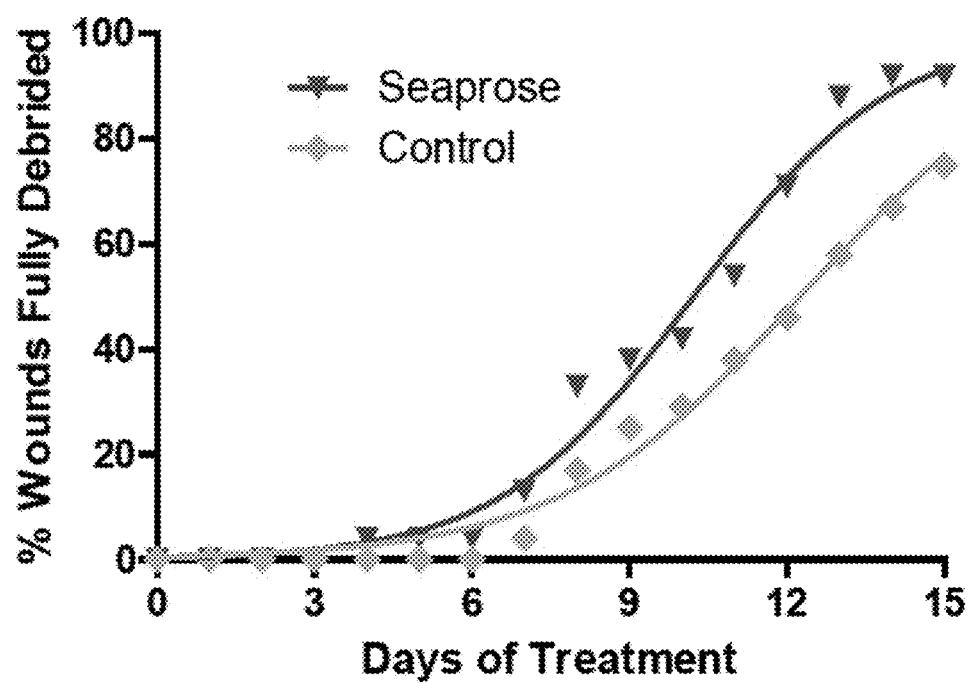
FIG. 3. A graph of the results of the in-vivo pig study comparing the debridement of wounds with Seaprose hydrogel compared with a control (moist wound care).

In this in vivo pig study, eschars were formed on the backs of pigs by introducing burn wounds using heated brass rods and allowing the formation of dry eschars over several days. There was a visual effect of Seaprose (SAP) on many wounds in comparison to control after one day of treatment (FIG. 2). Overall, SAP exhibited more rapid complete debridement of the eschars when compared against a control (non-adherent pre-moistened wound dressing with saline) (FIG. 3).

The particulars of this in vivo study are as follows. Pigs were anesthetized, the torso shaved with clippers and a razor, and washed with vedadine. Then an isopropyl rinse was performed to sterilize the surgical field. Twenty 2-cm wounds were created on the dorsum of each pig. The wounds were created using solid brass rods, heated to 100° C. in sand baths, held on the skin for 45 seconds. The wounds were left to dry for five days, giving the eschars time to form, with protective foam dressings being replaced every other day during eschar formation. After eschar formation and on a daily basis for treatments, the wounds were cleaned, photographed, treated according to the treatment randomization scheme, and dressed with non-adherent dressings (pre-moistened with saline) secured with Transpore tape and occlusive secondary dressings. Statistical significance for the number of eschars fully debrided was determined using Fisher's Exact test.

Treatment regimen for this study included use of a Seaprose containing formulation prepared in the following manner and a control which consisted of a non-adherent pre-moistened wound dressing with saline): (1) Seaprose S powder was prepared (see Table 7 below) and 100 mg of said powder was directly applied to the wound; and (2) a gel was prepared (see Table 8 below) and 400 mg of said gel was applied on top of the Seaprose S powder. Treatments were performed once a day for a fifteen day period. After the initial 24 hours of treatment, visual differences were apparent for many Seaprose-treated wounds, including pitting of the eschar and in some cases limited exposure of healthy wound tissue (FIG. 2). Over the fifteen day treatment period, Seaprose treatment produced a consistent trend of complete debridement of more wounds than the control (Seaprose treatment achieved statistical significance (p<0.05) versus the control on day 13 of treatment) (FIG. 3).

TABLE 7

| Seaprose S Powder* | |
|---|---|
| Ingredient | % Concentration (by weight) |
| SEAPROSE S | 2.0 |
| Sorbitol | 98.0 |
| TOTAL | 100 |

*Process: Seaprose S and soibitol were mixed at room temperature (approximately 20 to 25° C.) to obtain a homogenous powder.

TABLE 8

| Gel* | |
|---|---|
| Ingredient | % Concentration (by weight) |
| Hispagel-200 | 31.86 |
| Tris Buffer Solution 10 mM (pH 7.5) | 58.37 |
| Imidurea | 0.14 |
| Glycerin | 9.45 |
| Methylparaben | 0.16 |
| Propylparaben | 0.02 |
| TOTAL | 100 |

*Process: Preservatives were mixed in Tris Buffer at high temperature (>70° C.) along with glycerin. Upon cooling, Hispagel-200 was added. Clear and transparent gel was obtained.

REFERENCES

Publications

Bracale G. and Selvetella L. Clinical Study of The Efficacy of and Tolerance to Seaprose S in Inflammatory Venous Disease. *Minerva Cardioangiol.* 1996;44(10):515-524. (ABSTRACT).

Braga P. C., Moretti M., Piacenza A., Montoli C. C. and Guffanti E. E., Effects of Seaprose on the Rheology of Bronchial Mucus in Patients with Chronic Bronchitis. *Int J Clin Pharmacol Res.* 1993; 13(3):179-185.

Braga P. C., Rampoldi C., Ornaghi A., Caminiti, G., Beghi, and Allegra L. In Vitro Rheological Assessment of Mucolytic Activity Induced by Seaprose. *Pharmacol Res.* 1990;22(5):611-617.

Dindelli M, Potenza M. T., Candotti G., Frigerio L. and Pifarotti G. Clinical Efficacy and Tolerability of Seaprose S in the Treatment of Surgical Wound Complications in Puerperium. *Minerva Ginecologica* (1990) 42(7-8), 313-5.

Fossati A. Antiinflammatory Effects of Seaprose-S on Various Inflammation Models. *Drug Exp Clin Res.* 1999;25 (6):263-270.

Luisetti M., Piccioni P. D., Dyne K., Donnini M., Bulgheroni A., Pasturenzi L., Donnetta A. M., and Peona V. Some Properties of The Alkaline Proteinase from *Aspergillus Melleus*. *International Journal of Tissue Reactions* 13/4, 187-92 1991.

Miyazaki M, Tateishi H and Okuno Y. Clinical Use of Anti-inflammatory Enzyme, Sa-001 (Jeoase) in Pharyngolaryngeal Complications after Intratracheal Intubation. *Masui, the Japanese Journal of Anesthesiology*. (1969), 18(8), 722-30.

Moretti M., Bertoli E., Bulgarelli S., Testoni C., Guffanti E. E., Marchioni C. F. and Braga P. C. Effects of Seaprose on Sputum Biochemical Components in Chronic Bronchitic Patients: A Double-Blind Study vs. Placebo. *Int J Clin Pharmacol Res.* 1993;8(5):275-280.

Morihara K., Oka T. and Tsuzuki H. Comparative Study of Various Serine Alkaline Proteinases from Microorganisms. Esterase Activity Against N-Acylated Peptide Ester Substrates. *Arch. Biochem. Biophys.* 165 (1974) 72-79.

Nakatani H., Fujiwake H. and Hiromi K. Interaction of *Asp. melleus* Semi-alkaline Protease with Benzeneboronic Acid. *J Biochem.* 1977 May;81(5):1269-72. (ABSTRACT).

Spadari S., Subramanian A. R. and Kalnitsky G., Highly Restricted Specificity of The Serine Proteinase Aspergillopeptidase B. *Biochim. Biophys. Acta* 359 (1974) 267-272.

Turková J., Mikes O., Hayashi K., Danno G. and Polgár L. Alkaline Proteinases of the Genus *Aspergillus. Biochim. Biophys. Acta* 257 (1972) 257-263.

Drug Information Sheet: Jeoase Tablets 15 mg. Revised: March 2008.

US PATENT DOCUMENTS

U.S. Pat. No. 4,197,291 Klein et al.
U.S. Pat. No. 5,902,600 Woller et al.
U.S. Pat. No. 6,172,219 Callegaro et al.
U.S. Pat. No. 6,399,092 Hobson et al.
U.S. Pat. No. 6,479,060 Jones et al.
U.S. Pat. No. 6,548,556 Hobson et al.
U.S. Pat. No. 7,459,155 Margolin et al.
U.S. Pat. No. 7,642,079 Cayouette et al.
U.S. Pat. No. 7,785,584 Jones et al.
U.S. Patent Application 2003/0026794 Fein
US Patent Application 2003/0198631 Shi et al.
US Patent Application 2003/0198632 Shi et al.
US Patent Application 2010/0124549 Studin
US Patent Application 2010/0254968 Desser et al.

FOREIGN PATENT DOCUMENTS

WO 2008/019417
PCT/US10/59409
JP 56092217A (ABSTRACT)

The invention claimed is:

1. A method of debriding a wound that includes necrotic tissue, the method comprising applying to the wound a composition comprising a semi-alkaline protease produced by the fermentation of the fungus *Aspergillus melleus* (Seaprose), wherein application of the composition debrides necrotic tissue in the wound.

2. The method of claim 1, wherein the necrotic tissue is an eschar.

3. The method of claim 1, wherein the composition is topically applied to the wound.

4. The method of claim 1, wherein the composition further comprises a pharmaceutically acceptable topical carrier.

5. The method of claim 1, wherein the wound is a chronic wound.

6. The method of claim 5, wherein the chronic wound is a diabetic foot ulcer, a venous leg ulcer, an arterial leg ulcer, a decubitus ulcer, a stasis ulcer, a dermal ulcer, a burn, or a pressure ulcer.

7. The method of claim 1, wherein the composition includes 0.1 to 8% by weight of Seaprose.

8. The method of claim 7, wherein the composition includes 0.5 to 1.5% by weight of Seaprose.

9. The method of claim 1, wherein the Seaprose is isolated or purified Seaprose.

10. The method of claim 1, wherein the composition is formulated as a gel, cream, or ointment.

11. The method of claim 1, wherein the composition further comprises glycerin polyacrylate clatharate, glycerin, hydroxyethylcellulose, an emulsifying wax, or petrolatum, or any combination thereof.

12. The method of claim 1, wherein the composition is injected into the wound.

13. The method of claim 12, wherein the composition further comprises a pharmaceutically acceptable injectible carrier.

14. The method of claim 1, wherein the semi-alkaline protease has a molecular weight of about 31 kDa.

15. The method of claim 1, wherein the composition does not include any other enzymatic debridement agents other than Seaprose.

* * * * *